(12) United States Patent
Zhang et al.

(10) Patent No.: US 9,700,850 B2
(45) Date of Patent: Jul. 11, 2017

(54) ION EXCHANGE MEMBRANES CONTAINING INORGANIC PARTICLES

(71) Applicant: General Electric Company, Schenectady, NY (US)

(72) Inventors: Kai Zhang, Singapore (SG); John H. Barber, Guelph (CA); Russell James MacDonald, Westborough, MA (US); Yongchang Zheng, Westborough, MA (US); Li May Goh, Singapore (SG); Yan Gao, St-Romuald (CA); Yonghong Zhao, Singapore (SG)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/783,873

(22) PCT Filed: Apr. 12, 2013

(86) PCT No.: PCT/US2013/036338
§ 371 (c)(1),
(2) Date: Oct. 12, 2015

(87) PCT Pub. No.: WO2014/168628
PCT Pub. Date: Oct. 16, 2014

(65) Prior Publication Data
US 2016/0067654 A1    Mar. 10, 2016

(51) Int. Cl.
| | | |
|---|---|---|
| *B01D 69/12* | (2006.01) | |
| *C08J 5/22* | (2006.01) | |
| *H01M 8/10* | (2016.01) | |
| *H01M 8/103* | (2016.01) | |
| *H01M 8/1051* | (2016.01) | |

(52) U.S. Cl.
CPC .......... *B01D 69/125* (2013.01); *C08J 5/2231* (2013.01); *C08J 5/2275* (2013.01); *H01M 8/103* (2013.01); *H01M 8/1051* (2013.01); *Y02E 60/521* (2013.01); *Y02P 70/56* (2015.11)

(58) Field of Classification Search
CPC ..... B01D 69/125; C08J 5/2231; C08J 5/2275; H01M 8/103; H01M 8/1051; Y02P 70/56; Y02E 60/521
USPC .......................................................... 521/27
See application file for complete search history.

(56) References Cited

U.S. PATENT DOCUMENTS

| | | | |
|---|---|---|---|
| 3,457,171 A | 7/1969 | Flowers et al. | |
| 5,264,125 A | 11/1993 | MacDonald et al. | |
| 7,357,999 B2 | 4/2008 | Kim | |
| 7,429,280 B2 | 9/2008 | Biegert et al. | |
| 7,968,663 B2* | 6/2011 | MacDonald | B01J 41/14 526/304 |
| 9,227,187 B2* | 1/2016 | Bigarre | H01B 1/122 |
| 2008/0102339 A1* | 5/2008 | Galiano | B01D 67/0079 429/483 |
| 2010/0196786 A1* | 8/2010 | Niepceron | B82Y 30/00 429/483 |
| 2012/0024786 A1 | 2/2012 | Nasr et al. | |
| 2012/0107720 A1 | 5/2012 | Nasr et al. | |
| 2012/0172461 A1 | 7/2012 | Tsai et al. | |
| 2014/0113982 A1 | 4/2014 | Bigarre et al. | |

FOREIGN PATENT DOCUMENTS

FR    2967925 A1    6/2012

OTHER PUBLICATIONS

Yang et al., "Exfoliated Graphite Oxide Decorated by PDMAEMA Chains and Polymer Particles", Langmuir, vol. No. 25, Issue No. 19, pp. 11808-11814, Jul. 14, 2009.
Lian et al., "Enhanced Electromechanical Performance of Graphite Oxide-Nafion Nanocomposite Actuator", The Journal of Physical Chemistry C, vol. No. 114, Issue No. 21, pp. 9659-9663, May 13, 2010.
Gao et al.,"Engineered Graphite Oxide Materials for Application in Water Purification", ACS Applied Materials & Interfaces, vol. No. 3, Issue No. 6, pp. 1821-1826, May 13, 2011.
Kumar et al., "A Graphite Oxide Paper Polymer Electrolyte for Direct Methanol Fuel Cells", International Journal of Electrochemistry, vol. No. 2011, Article ID 434186, pp. 7, 2011.
Zarrin et al., "Functionalized Graphene Oxide Nanocomposite Membrane for Low Humidity and High Temperature Proton Exchange Membrane Fuel Cells", The Journal of Physical Chemistry C, vol. No. 115, Issue No. 42, pp. 20774-20781, Sep. 14, 2011.
Kumar et al., "Graphite Oxide/Nafion Composite Membranes for Polymer Electrolyte Fuel Cells", RSC Advances, vol. No. 2, Issue No. 23, pp. 8777-8782, Jul. 26, 2012.
PCT Search Report and Written Opinion issued in connection with corresponding Application No. PCT/US2013/036338 on Jan. 15, 2014.

* cited by examiner

*Primary Examiner* — Michael M Bernshteyn

(57) ABSTRACT

An ion exchange membrane and a method of making it. The membrane may be used, for example, in an electrodialysis module or electrochemical cell. The membrane comprises an ion exchange polymer and inorganic particles preferably linked to the ion exchange polymer. To make a membrane, inorganic particles are mixed into an ion exchange membrane pre-cursor. A polymerization initiator or catalyst is then added and the resulting mixture is placed in a form and cured. The inorganic particles may comprise, for example, an oxidized form of graphite such as graphite oxide. The ion exchange polymer may comprise an ionic monomer, containing a quaternary ammonium group for anion exchange or a sulfonate group for cation exchange, along with a cross-linking co-monomer containing polymerizable diacrylic functionalities. The membrane is self-supporting and can be made without a supporting fabric.

8 Claims, No Drawings

ION EXCHANGE MEMBRANES CONTAINING INORGANIC PARTICLES

BACKGROUND

This specification relates to membranes, particularly ion exchange membranes.

Ion exchange membranes may be used to treat and remove ionizable components from fluids for a variety of applications. The ion exchange functionality operates to transport one type of ion across an ion exchange polymer in an electric field, while substantially or effectively blocking most ions of the opposite polarity. For example, anion exchange polymers carry cationic groups, which repel cations and are selective to anions.

Anion exchange polymers may be prepared from tertiary amines, which are quaternized to provide anionic functionality. The quaternary ammonium compounds are crosslinked and polymerized to form anion exchange polymers. Typical methods for making anion exchange polymers require the use of alkyl halides for quaternizing the anion exchange polymer.

U.S. Pat. No. 7,968,663 provides another example of an anion exchange polymer that can be used to make a membrane. The polymer is made by reacting a tertiary amine, an acid inhibitor and a polyepoxide to form a quaternary ammonium monomer in the presence of a catalyst. The exchange polymer is prepared without using alkyl halides.

An ion exchange membrane is made by embedding a membrane dope in a stable reinforcing fabric. The reinforcing fabric is typically made from a textile polymer such as polypropylene, polyester, polyvinyl chloride or polyethylene. The dope may comprise an ionic monomer containing a quaternary ammonium group (anion exchange) or a sulfonate group (cation exchange) along with a crosslinking co-monomer containing polymerizable diacrylic functionalities. The reinforcing fabric determines the thickness of the membrane. The fabric is typically pre-treated to improve its wettability and compatibility with the ion-exchange polymer but the pre-treatment may introduce contaminants into a membrane.

SUMMARY OF THE INVENTION

This specification describes an ion exchange membrane and a method of making it. The membrane may be used, for example, in an electrodialysis module or electrochemical cell.

An ion exchange membrane comprises an ion exchange polymer and inorganic particles. In an embodiment, the inorganic particles are linked to the ion exchange polymer. In a method of making an ion exchange membrane, inorganic particles are mixed into an ion exchange membrane pre-cursor. A polymerization initiator or catalyst is added and the resulting mixture is placed in a form and cured.

In the membrane and the method of making it, the inorganic particles may comprise, for example, an oxidized form of graphite such as graphite oxide, graphene oxide or partially reduced graphene oxide. The ion exchange polymer may comprise an ionic monomer, containing a quaternary ammonium group for anion exchange or a sulfonate group for cation exchange, along with a crosslinking co-monomer containing polymerizable diacrylic functionalities.

In an embodiment, the membrane is self-supporting and can be made without a supporting fabric. In this case, the thickness of the membrane can be controlled without being limited by the thickness of a suitable fabric. Avoiding the fabric also avoids possible contamination of the ion exchange polymer with contaminants or wetting agents on the fabric.

DETAILED DESCRIPTION

The singular forms "a," "an" and "the" include plural referents unless the context clearly dictates otherwise. The endpoints of all ranges reciting the same characteristic are independently combinable and inclusive of the recited endpoint. All references are incorporated herein by reference.

The modifier "about" used in connection with a quantity is inclusive of the stated value and has the meaning dictated by the context (e.g., includes the tolerance ranges associated with measurement of the particular quantity).

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

An ion exchange membrane, to be described in greater detail below, may be used in electrodialysis (ED), electrochemical cell, or other ion exchange membrane cell equipment. ED devices include electrodialysis reversal devices and supercapacitive discharge devices. ED devices can be used to remove ions from water.

The ion exchange membrane is optionally a self-supporting homogenous membrane. The membrane may be used without a supporting fabric. A network of inorganic particles supports the membrane in place of, or in addition to, a supporting fabric. The inorganic particles are linked to the ion exchange polymer by a chemical bond, for example C—O or N—O bonds, or by a physical bond, for example hydrogen bonding or π-π stacking.

Some existing methods for the preparation of ion-exchange membranes involve polymerizing an ionic monomer along with a crosslinking co-monomer containing polymerizable diacrylic functionalities. The ionic monomer may contain a quaternary ammonium group for anion exchange or a sulfonate group for cation exchange. Similar compounds may also be used to create an ion exchange polymer as further described in this specification. However, inorganic particles are added to a mixture of the compounds before they are reacted into the ion exchange polymer. A polymerization catalyst or initiator is added after the inorganic particles. The resulting mixture is formed into a sheet and cured, typically thermally or photochemically. For example, the mixture may be formed into a sheet between two glass plates. Alternatively, the membrane sheet may be formed between two flexible sheets of a barrier material sealed at their edges and pulled through a pair of nip rollers. In this case, the mixture added between the barrier material sheets upstream of the nip of the rollers.

The inorganic particles may be, for example, an oxidized derivative of graphite such as graphite oxide, graphene oxide or partially reduced graphene oxide. In an embodiment, the inorganic particles are added to the ion exchange polymer at a ratio of between 1 and 20 wt %. The inorganic particles contain functional groups and are linked with the ion-exchange polymer by chemical functionalization. The inorganic particles may also have interactions between themselves, for example hydrogen bonding or π-π stacking between particles of graphene oxide. Optionally, the cured ion exchange membrane may be self-supporting without a reinforcing fabric added. In this case, the thickness (and therefore the resistance) of the ion-exchange membrane can be controlled or selected without being limited to the thicknesses of available reinforcing fabrics. A self-supporting membrane also avoids the possibility of the ion exchange polymer reacting with a contaminant or wetting agent on the reinforcing fabric.

The membrane, and the method of making it, may be similar to the polymers and methods described in U.S. Pat. No. 7,968,663 issued on Jun. 28, 2011 to Russell MacDonald et. al., which is incorporated by reference. However, the inorganic particles are added before the membrane is polymerized.

In general, a method for making an anion exchange polymer comprises reacting a tertiary amine, an acid inhibitor and a polyepoxide to form a quaternary ammonium monomer and polymerizing the quaternary ammonium monomer in the presence of inorganic particles and a catalyst.

The tertiary amine may be an ethylenic tertiary amine. In one embodiment, the ethylenic tertiary amine is selected from the group consisting of dimethylaminopropylmethacrylamide (DMAPMA), dimethylaminopropylacrylamide (DMAPAA), diethylaminopropylmethacrylamide (DEAPMA), dimethylaminoethylmethacrylate (DMAEMA) and mixtures thereof. In another embodiment, the ethylenic tertiary amine monomer is DMAPMA. In an embodiment, a tertiary amine is DMAPMA.

The polyepoxide may be any type of polyepoxide having at least two epoxide groups. In one embodiment, the polyepoxide is a diglycidyl ether or a triglycidyl ether. Diglycidyl ethers include, but are not limited to, diethylene glycol diglycidyl ether, diglycidyl 1,2-cyclohexanedicarboxylate, N,N-diglycidyl-4-glycidyloxyaniline, bisphenol A diglycidyl ether, brominated bisphenol A diglycidyl ether, bisphenol F diglycidyl ether, 1,4-butanediol diglycidyl ether, 1,4-butanediyl diglycidyl ether, 1,4-cyclohexanedimethanol diglycidyl ether, glycerol diglycidyl ether, resorcinol diglycidyl ether, bis[4-(glycidyloxy)phenyl]methane, bisphenol A propoxylate diglycidyl ether, dimer acid diglycidyl ester, ethylene glycol diglycidyl ether, brominated neopentyl glycol diglycidyl ether, diglycidyl ether-terminated poly(dimethylsiloxane), poly(ethylene glycol)diglycidyl ether, poly(propyleneglycol)diglycidyl ether, 1,2,3-propanetriol glycidyl ether and 1,3-butanediol diglycidyl ether. Triglycidyl ethers include, but are not limited to, tris(2,3-epoxypropyl)isocyanurate, trimethylolpropane triglycidyl ether, tris(4-hydroxyphenyl)methane triglycidyl ether 2,6-tolylene diisocyanate, tris(4-hydroxyphenyl)methane triglycidyl ether, glycerol propoxylate triglycidyl ether and trimethylolethane triglycidyl ether.

In another embodiment, the polyepoxide is a diepoxide. Diepoxides include, but are not limited to, 1,3-butadienediepoxide, 1,3-butadiene diepoxide, dicyclopentadiene dioxide, methyl cis,cis-11,12;14,15-diepoxyeicosanoate.

The quaternization is conducted in the presence of an acid inhibitor, which controls the polyepoxide from self-polymerization. The acid inhibitor prevents the polyepoxide from self-polymerizing by quenching the reaction. The amount of quenching is controlled by the amount of acid inhibitor used in the reaction. The acid inhibitor may be any type of acid. In one embodiment, the acid inhibitor is a mineral acid. In another embodiment, the acid inhibitor includes, but is not limited to, hydrochloric acid, methane sulfonic acid, sulfuric acid or phosphoric acid. The acid inhibitor is added in any amount suitable for quenching the polyepoxide. In one embodiment, the acid inhibitor is present in an amount of from about 75 percent by mole weight to about 125 percent by mole weight, based on the mole weight of the tertiary amine. In another embodiment, the acid inhibitor is present in an amount of from about 75 percent by mole weight to about 100 percent by mole weight, based on the mole weight of the tertiary amine.

The anion exchange polymer may be synthesized using a wide ratio range of the tertiary amine to the polyepoxide. In one embodiment, the ratio is from about 0.3 to about 1.5 moles of the tertiary amine to each equivalent mole of the polyepoxide. In another embodiment, the ratio is from about 0.5 to about 1.0 moles of the tertiary amine monomer per equivalent mole of the polyepoxide.

For example, a tertiary amine containing acrylic monomer such as DMAPMA may be reacted, in the presence of an acid, with an epoxy-containing compound such as CHDM-DGE to generate a diacrylic monomer containing quaternary ammonium groups.

An ionic, self-crosslinking, diacrylic monomer is then polymerized in the presence of a non-crosslinking, non-ionic co-monomer such as N-vinyl caprolactam (V-Cap) and inorganic particles via initiator catalyzed free radical polymerization. These reactions result in ion exchange polymers and materials.

The catalysts may be spontaneously activated or activated by heat, electromagnetic radiation, electron beam radiation or by chemical promoters. The catalyst may be added in any amount suitable for aiding in polymerization. In one embodiment, the catalyst is in an amount of from about 0.1 to about 5.0 percent by weight of the reaction mixture.

The catalyst may be any type of catalyst suitable for polymerizing the quaternary ammonium monomer. In one embodiment, the catalyst is a peroxide. The peroxide includes, but is not limited to, methyl ethyl ketone peroxide and dibenzoyl peroxide. In another embodiment, the catalyst is a water soluble or oil soluble azo initiator. The azo initiator includes, but is not limited to, 2,2'-azobis[2-(2-imidazolin-2-yl)propane]dihydrochloride, 2,2'-azobis(N,N'-dimethylene isobutyramidine)dihydrochloride, 2,2'-azobis(2-methylpropionamidine)dihydrochloride, 2,2'-azobis[N-(2-carboxyethyl)-2-methylpropionamidine]hydrate, 2,2'-azobis {2-[1-(2-hydroxyethyl)-2-imidazolin-2-yl)propane], 2,2'-azobis[2-methyl-N-(2-hydroxyethyl)propionamide] and dimethyl 2,2'-azobis(2-methylpropionate).

In one embodiment, the components are combined in the presence of a solvent. Any solvent is suitable for use in this embodiment, so long as the solvent is not itself polymerizable and the components are soluble in it. Solvents suitable in this embodiment include, but are not limited to, water, polyethylene glycols, dimethylsulfoxide, 2-pyrrolidone, N-methyl pyrrolidone and mixtures thereof.

The amount of solvent is added in any amount suitable for solubilizing the components. In one embodiment, the amount of solvent is from about 10 to about 90 percent by weight based on the total weight of the reaction mixture. In another embodiment, the amount of solvent is from about 20 to about 70 percent by weight based on the total weight of the reaction mixture. In another embodiment, the amount of solvent is from about 25 to about 50 percent by weight based on the total weight of the reaction mixture.

Additionally, other ethylenic monomers may be added to the polymerization mixture to increase or decrease the ion exchange capacity of the resulting ion exchange polymer. Examples of ethylenic monomers that lower the ion exchange capacity include, but are not limited to, methacrylamine, N-methylmethacrylamide, N-vinyl pyrrolidinone and N-vinyl caprolactam. Examples of ethylenic monomers that raise the ion exchange capacity include, but are not limited to, methacrylamidopropyl trimethylammonium chloride (MAPTAC) and trimethylammoniumethyl methacrylate chloride (TMAEMC).

These ethylenic monomers may be added to the reaction mixture with the other reactants and may be added in any order with the reactants. The ethylenic monomers may be added in any amount suitable for affecting the ion exchange capacity of the ion exchange polymer. In one embodiment, the ethylenic monomer is added in an amount of from about 0 to about 50 molar percent of the tertiary amine. In another embodiment, the ethylenic monomer may be added in an amount of from about 10 to about 40 molar percent of the tertiary amine. In another embodiment, the ethylenic monomer may be added in an amount of from about 20 to about 40 molar percent of the tertiary amine.

An ion exchange membrane was obtained in U.S. Pat. No. 7,968,663 by polymerizing the mixture on a reinforcing fabric. In the present case, inorganic materials are added to the mixture before it is polymerized. For example, a diacrylic monomer as described above may be mixed with 1-20% of an oxidized graphite derivative such as graphite oxide (GO). The mixing may be done at room temperature. The resulting mixture is formed, for example by casting the mixture between two plastic sheets in a stationary (for example between glass plates) or continuous (while passing the plastic sheets between a pair of nip rollers) process. The thickness of the casting layer may be controlled by one or more gaskets added between the plastic sheets or to adjustments to the gap between rollers, line speed or mixture feed rate of a continuous process. The membrane is cured after it is formed and optionally post treated, for example by rinsing. The plastic sheets may be made, for example, polyethylene, polypropylene or Teflon™.

A similar process is described in U.S. Pat. No. 5,264,125, entitled Process for Manufacturing Continuous Supported Ion Selective Membranes Using Non-Polymerizable High Boiling Point Solvents, which is incorporate by reference. In that patent, a process comprises forming a sandwich of a substrate and a pliable film on each face of the substrate. However, when making an ion exchange polymer with inorganic particles as described above, it substrate can be omitted. The edges of the films are sealed together to form a pocket. Subsequently, the films are pulled between a pair of squeeze rolls. A liquid is added to the pocket above the squeeze rolls to form a pool of the liquid above the squeeze rolls and between the films. Some of the liquid passes with the films through the squeeze rolls. From the squeeze rolls, the films pass through a set of means, for example heaters, for curing the liquid. Polymerizable components in the liquid are polymerized thereby forming a polymer sheet. The films proceed through a set of knives which remove the seals at the edges of the films and through a pair of rollers which remove the films from the polymer sheet. The polymer sheet is then an ion exchange membrane.

The inorganic materials in the membrane can make it strong enough for use as self-supporting membrane without extra reinforcing materials in some applications. The co-monomer, such as V-Cap or glycidyl methacrylate (GMA), an excess of the polyepoxide such as CHDMDGE left over after reaction with the primary monomer, or an additional ethylenic monomer with reactive groups such as isocyante may be used to links to the inorganic particles.

In one example, V-Cap or GMA or another co-monomer is used in combination with an ionic cross linked product of DMAPMA and CHDMDGE having the structure shown below:

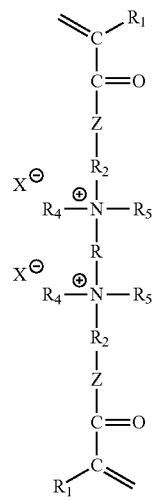

wherein R is $-[CH_2-CH(OH)]_2-W$; $R_1$ is hydrogen or a $C_1$-$C_{12}$ alkyl group; Z is oxygen or N—$R_3$; $R_2$ is $-[CH_2]_n-$; $R_3$ is hydrogen or $-[CH_2]_m-CH_3$; $R_4$ and $R_5$ are each, independently, $-[CH_2]_m-CH_3$; X is selected from the group consisting of Cl, Br, I and acetate; W is a bridging group or atom; m is an integer from 0 to 20; and n is an integer from 1 to 20.

In another example, the membrane comprises a product of 1 molecule of mono-tertiary amine DMAPMA and one molecule of di-epoxy CHDMDGE. The resulting ionic monomer has an epoxy group that can link onto graphite oxide or a derivative form or graphite oxide. The structure of the monomer is shown below:

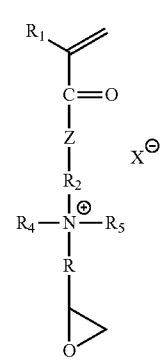

wherein R is $-[CH_2-CH(OH)]-W-$; $R_1$ is hydrogen or a $C_1$-$C_{12}$ alkyl group; Z is oxygen or N—$R_3$; $R_2$ is $-[CH_2]_n-$; $R_4$ and $R_5$ are each, independently, $-[CH_2]_m-CH_3$; $R_3$ is hydrogen or $-[CH_2]_m-CH_3$; X is selected from the group consisting of Cl, Br, I and acetate; W is a bridging group or atom; m is an integer from 0 to 20; and n is an integer from 1 to 20.

The thickness of the self-supporting membrane can be, for example, between 0.1 mm and 0.7 mm. In some cases, the membrane may be thinner than a fabric supported membrane and therefore have reduced resistance. The ion exchange capacity (IEC) of the membrane can be controlled by varying the stoichiometric amounts of the polymerizing reactants. The membrane water uptake can be regulated by changing the weight percent of water in the mixture before it is formed into a membrane. Typical theoretical IEC values for the membrane vary between 1 and 2.4 meq/g and the theoretical water uptake value is in the range of 30% and 42%.

It is expected that similar membranes may be made involving other ion exchange polymers. For example, polymers maybe made from other ionic monomers, for example monomers containing a quaternary ammonium group for anion exchange or a sulfonate group for cation exchange. These ionic monomers may be polymerized along with a crosslinking co-monomer containing polymerizable diacrylic functionalities. However, inorganic particles are added before initiating the crosslinking reaction.

Optionally, a self-supporting ion-exchange membrane may have a thickness between 0.1 mm and 0.3 mm or 0.4 mm. At this thickness, the membrane has lower resistance per unit area than a typical supported membrane. Using these membranes in an electrodialysis (ED), for example an electrodialysis reversal (EDR), stack would reduce the energy consumption of the stack. The self-supporting ion-exchange membrane needs only a simple post-treatment process such as rinsing with water. When a reinforcing fabric is not used, it is not necessary to post-treat the membrane to remove contaminants from the fabric. The raw materials cost of a membrane could also be reduced, for example by about 30%, due to the thinner membrane requiring less of the ion exchange polymer.

In an embodiment, the inorganic particles are an oxidized derivative of graphite such as graphite oxide, graphene oxide, or partially reduced graphene oxide. It is possible that other particles might be used. However, the particles are more particularly, an insulator or semiconductor, compatible with ionomer polymers, and stable in caustic and chlorine solutions. For example, activated carbon particles would be too highly conductive and could cause a risk of shorting out an ED stack. However, silicate or zeolite particles might be used.

In order that those skilled in the art will be better able to practice the present disclosure, the following examples are given by way of illustration and not by way of limitation.

EXAMPLES

In a first example, an ion exchange membrane was made using DMAPMA, hydrochloric acid (HCl), CHDMDGE, water and glycidyl methacrylate (GMA). The mass and molecular weight of each of these compounds is as follows: DMAPMA—25.75 g, MW 170.25; HCl—15.8 g, MW 36.5; CHDMDGE—256.34 g, MW 18.5 g; H2O—34.4 g, MW 18; GMA—5.6 g, MW 142.1. The membrane also included 5 g of graphite oxide. A membrane dope was produced by first mixing the DMAPMA and water. The hydrochloric acid was added to this mixture while stirring at a slow rate of addition to keep the temperature below 50 degrees C. The CHDMDGE was added and the resulting mixture heated to 75 degrees C. for 30 minutes. This mixture was then cooled to room temperature and the GMA was added. 5 g of graphite oxide was added and this resulting mixture was stirred for one day. An initiator (VA-044) was then added and stirred into the mixture.

To prepare a membrane, a sheet of Mylar™ was placed on a glass plate. A gasket was placed on the sheet. The gasket was filled with the mixture produced above. The gasket was then covered with another sheet of Mylar™ and a second glass plate. The edges of the glass plates were clamped together and the membrane was cured for one hour at 85 degrees C. The membrane was removed from the glass plates and Mylar™ sheets and treated by soaking in 1N NaCl solution.

The cured membrane was tested and had the following characteristics: ion exchange capacity—2.3 meq/g; water content—35.9%; thickness—0.36 mm; resistance—15.3 Ohm-cm2.

In a second example, an ion exchange membrane was made using DMAPMA, hydrochloric acid (HCl), CHDMDGE, water and N-vinyl caprolactam (V-Cap). The mass and molecular weight of each of these compounds is as follows: DMAPMA—25.75 g, MW 170.25; HCl—15.8 g, MW 36.5; CHDMDGE—256.34 g, MW 18.5 g; H2O—34.4 g, MW 18; V-Cap—5.6 g, MW 139.19. The membrane also included 5 g of graphite oxide. A membrane dope was produced by first mixing the DMAPMA and water. The hydrochloric acid was added to this mixture while stirring at a slow rate of addition to keep the temperature below 50 degrees C. The CHDMDGE was added and the resulting mixture heated to 75 degrees C. for 30 minutes. This mixture was then cooled to room temperature and the V-Cap added. 5 g of graphite oxide was added and this resulting mixture was stirred for one day. An initiator (VA-044) was then added to the mixture with stirring for 30 minutes.

To prepare a membrane, a sheet of Mylar™ was placed on a glass plate. A gasket was placed on the sheet. The gasket was filled with the mixture produced above. The gasket was then covered with another sheet of Mylar™ and a second glass plate. The edges of the glass plates were clamped together and the membrane was cured for one hour at 85 degrees C. The membrane was removed from the glass plates and Mylar™ sheets and treated by soaking in 1N NaCl solution.

The cured membrane was tested and had the following characteristics: ion exchange capacity—2.39 meq/g; water content—39.5%; thickness—0.4 mm; resistance—12.6 Ohm-cm2.

Both of the membranes had sufficient strength to be self-supporting membranes and would be useful in an ED (including EDR) cell without a supporting fabric. The membrane made using V-cap was more brittle and had lower tensile strength that the membrane made using GMA. We believe that the GMA forms chemical bonds between the ionic polymer and the GO particles while the V-cap forms only hydrogen bonds with surface groups on the GO particles. However, the membrane made using V-cap has lower resistance.

This written description uses examples to disclose the invention and also to enable any person skilled in the art to practice the invention. The patentable scope of the invention is defined by the claims, and may include other examples that occur to those skilled in the art.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for making an ion exchange membrane comprising polymerizing an ionic monomer, and optionally another, second compound, in the presence of inorganic particles to form the ion exchange membrane, the monomer or second compound linking to the inorganic particles by a physical or chemical bond, wherein the monomer or second compound links to the inorganic particles by a C—O or N—O chemical bond, hydrogen bonding or π-π stacking, and wherein the monomer or second compound is selected from the group consisting of a) ethylenic monomers, b) polyepoxides, c) N-vinyl caprolactam, d) glycidyl methacrylate and e) a reaction product of dimethylaminopropylmethacrylamide (DMAPMA) and 1,4-cyclohexanedimethanol diglycidyl ether (CHDMDGE).

2. The method of claim 1 wherein the monomer is a reaction product of dimethylaminopropylmethacrylamide (DMAPMA) and 1,4-cyclohexanedimethanol diglycidyl ether (CHDMDGE) having one of the following structures:

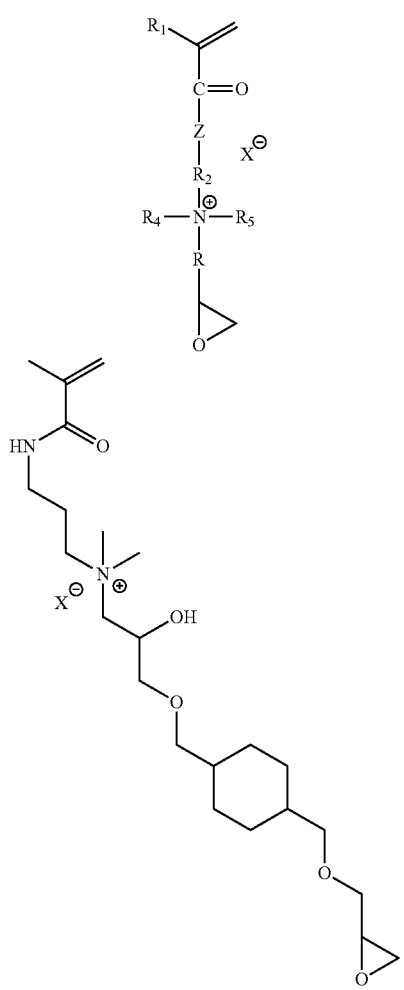

wherein R is —[$CH_2$—CH(OH)]—W—; $R_1$ is hydrogen or a $C_1$-$C_{12}$ alkyl group; Z is oxygen or N—$R_3$; $R_2$ is —[$CH_2$]$_n$—; $R_3$ is hydrogen or —[$CH_2$]$_m$—$CH_3$; $R_4$ and $R_5$ are each, independently, —[$CH_2$]$_m$—$CH_3$; X is selected from the group consisting of Cl, Br, I and acetate; W is a bridging group or atom; m is an integer from 0 to 20, and n is an integer from 1 to 20.

3. The method of claim 1 wherein the ionic monomer is polymerized along with a crosslinking co-monomer containing polymerizable diacrylic functionalities.

4. The method of claim 1 wherein the inorganic particles are added prior to a catalyst or initiator.

5. The method of claim 1 wherein the inorganic particles comprise an oxidized graphite derivative, a silicate or a zeolite.

6. The method of claim 1 wherein the inorganic particles comprise graphite oxide, graphene oxide or partially reduced graphene oxide.

7. The method of claim 1 comprising curing the polymer without a reinforcing fabric.

8. The method of claim 1 wherein the monomer has the following structure:

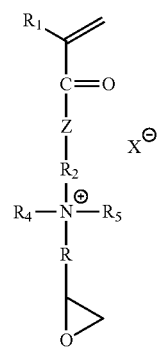

wherein R is —[$CH_2$—CH(OH)]—W—; $R_1$ is hydrogen or a $C_1$-$C_{12}$ alkyl group; Z is oxygen or N—$R_3$; $R_2$ is —[$CH_2$]$_n$—; $R_3$ is hydrogen or —[$CH_2$]$_m$—$CH_3$; $R_4$ and $R_5$ are each, independently, —[$CH_2$]$_m$—$CH_3$; X is selected from the group consisting of Cl, Br, I and acetate; W is a bridging group or atom; m is an integer from 0 to 20, and n is an integer from 1 to 20.

* * * * *